United States Patent
Sherman

(10) Patent No.: US 9,623,047 B2
(45) Date of Patent: Apr. 18, 2017

(54) COMPOSITION AND METHOD FOR IMPROVING GASTROINTESTINAL HEALTH OF EQUINE

(71) Applicant: James E. Sherman, Henrico, VA (US)

(72) Inventor: James E. Sherman, Henrico, VA (US)

(73) Assignee: Photo Finish Supplements, LLC, Phoenixville, PA (US)

( * ) Notice: Subject to any disclaimer, the term of this patent is extended or adjusted under 35 U.S.C. 154(b) by 518 days.

(21) Appl. No.: 14/133,800

(22) Filed: Dec. 19, 2013

(65) Prior Publication Data

US 2014/0186472 A1     Jul. 3, 2014

Related U.S. Application Data

(60) Provisional application No. 61/746,169, filed on Dec. 27, 2012.

(51) Int. Cl.

| | |
|---|---|
| *A23K 50/20* | (2016.01) |
| *A23K 10/18* | (2016.01) |
| *A23K 20/158* | (2016.01) |
| *A23K 20/22* | (2016.01) |
| *A23K 20/24* | (2016.01) |
| *A61K 35/747* | (2015.01) |
| *A61K 36/899* | (2006.01) |
| *A61K 33/10* | (2006.01) |
| *A61K 31/7016* | (2006.01) |
| *A61K 33/06* | (2006.01) |
| *A61K 36/31* | (2006.01) |
| *A61K 33/08* | (2006.01) |
| *A61K 9/70* | (2006.01) |
| *A23K 20/163* | (2016.01) |

(52) U.S. Cl.
CPC .............. *A61K 33/08* (2013.01); *A23K 10/18* (2016.05); *A23K 20/158* (2016.05); *A23K 20/163* (2016.05); *A23K 20/22* (2016.05); *A23K 20/24* (2016.05); *A23K 50/20* (2016.05); *A61K 9/7007* (2013.01); *A61K 31/7016* (2013.01); *A61K 33/06* (2013.01); *A61K 33/10* (2013.01); *A61K 35/747* (2013.01); *A61K 36/31* (2013.01); *A61K 36/899* (2013.01)

(58) Field of Classification Search
CPC ...... A23K 50/20; A23K 10/18; A23K 20/158; A23K 20/136; A23K 20/22; A23K 20/24; A61K 35/747; A61K 36/899; A61K 33/10; A61K 33/08; A61K 31/7016; A61K 33/06; A61K 36/31; A61K 9/7007

USPC ....... 424/693, 694, 283.1, 459; 426/53, 103, 426/68

See application file for complete search history.

(56) References Cited

U.S. PATENT DOCUMENTS

| | | | |
|---|---|---|---|
| 4,729,896 A * | 3/1988 | Sawhill | A23K 1/003 426/2 |
| 4,735,967 A | 4/1988 | Neesby | |
| 4,761,274 A | 8/1988 | Denick, Jr. et al. | |
| 4,853,230 A | 8/1989 | Lovgren et al. | |
| 4,920,129 A | 4/1990 | Shiokawa et al. | |
| 4,976,963 A | 12/1990 | Schricker et al. | |
| 5,461,082 A | 10/1995 | Machimura et al. | |
| 5,505,968 A * | 4/1996 | Schaefer | A23K 1/1631 424/617 |
| 5,578,576 A | 11/1996 | Leddin | |
| 5,908,634 A * | 6/1999 | Kemp | A23K 1/002 424/442 |
| 6,066,342 A | 5/2000 | Gurol et al. | |
| 6,645,988 B2 | 11/2003 | Phillips | |
| 2005/0037070 A1 | 2/2005 | Hall et al. | |
| 2005/0163867 A1 | 7/2005 | Schachtel | |
| 2005/0220870 A1 | 10/2005 | Hepburn et al. | |
| 2006/0135406 A1 | 6/2006 | Glozman et al. | |
| 2008/0050455 A1 | 2/2008 | Smith | |
| 2008/0214619 A1 | 9/2008 | Wolfe et al. | |
| 2010/0021430 A1* | 1/2010 | Baginski | A23K 1/009 424/93.3 |
| 2010/0233756 A1* | 9/2010 | Sunvold | A23K 1/003 435/34 |

OTHER PUBLICATIONS

ADM Media Relations, ADM Research Finds Corn Stover Can Be Effective in Cattle Feed with Simple on-Farm Treatment; Feb. 16, 2011.*

* cited by examiner

*Primary Examiner* — Michael G. Hartley
*Assistant Examiner* — Nabila Ebrahim
(74) *Attorney, Agent, or Firm* — Goodman Allen Donnelly PLLC; Matthew R. Osenga, Esq.

(57) ABSTRACT

A composition to moderate excessive and potentially harmful gastric acid levels in the gastrointestinal tract of horses is disclosed. The composition includes calcium oxide and/or calcium hydroxide, which may be in combination with various buffers and other ingredients such as sodium bicarbonate, sodium bentonite, sodium sesquicarbonate, calcium carbonate, magnesium oxide, omega-3 and omega-6 fatty acid sources, simple carbohydrates, and/or probiotics. A method of administering the composition is also disclosed.

1 Claim, 2 Drawing Sheets

COMPOSITION AND METHOD FOR IMPROVING GASTROINTESTINAL HEALTH OF EQUINE

CROSS-REFERENCE TO RELATED APPLICATION

This application claims the benefit of U.S. Provisional Application No. 61/746,169, filed Dec. 27, 2012, the contents of which are incorporated by reference.

FIELD OF THE INVENTION

The present invention relates generally to compositions and methods for improving the gastrointestinal health of equine, and more particularly to compositions and methods of increasing the pH within the stomachs of horses.

BACKGROUND OF THE INVENTION

Equine gastric ulcers can affect horses at any age. Up to 88 percent of racehorses and 59 percent of non-race horses are affected by equine gastric ulcers. Even foals and non-performance horses are not immune under some environmental and management conditions.

The stomach of the horse is made up of two distinct areas. The bottom is glandular and has an effective protective coating to protect it from the acid produced in that area. The upper portion functions as a mixer of the stomach contents and is not afforded the extensive acid protection mechanisms. It is most prone to ulcer development when exposed to more acidic conditions.

Horses evolved as grazing animals that were engaged in nearly continuous feeding activity. Therefore, a horse's stomach produces acid continuously and not only in response to stimulus from feeding. With extended time periods between feedings for stalled horses, the gastric pH may fall rapidly, contributing to the development of equine gastric ulcer syndrome (EGUS). Withholding feed for several hours from horses may depress gastric fluid pH to 2.0 or less.

EGUS may express itself both as a symptomatic and asymptomatic disease. The majority of horses with ulcers do not show outward symptoms. However, they may exhibit more subtle symptoms such as poor appetite, decreased athletic performance, weight loss, and a dull or rough hair coat. Horses with more severe cases of EGUS will show signs of abdominal pain (colic) and/or bruxism (grinding the teeth).

EGUS is often a man-made disease. Not only have feeding times often been reduced to twice daily, but the animals are fed higher nutrient-dense diets, leaving the horse with long periods of idle time between meals. Grain-rich diets contribute to increased volatile fatty acid production during the digestion process in the stomach, further contributing to EGUS.

The incidence of gastric ulcers can also be influenced by stress (environmental, dietary, and physical). The onset of race training, hauling, showing, or weaning may induce ulcer formation in as few as five to seven days.

Strenuous exercise is another contributing factor to EGUS. Activity that involves a tightening of the abdominal muscles causes an increase in intra-abdominal pressure. This increase in pressure forces a portion of the hydrochloric acid and bile acid normally found in the lower glandular region of the stomach upward into the squamous or non-glandular region of the stomach. This ultimately leads to gastritis and ulcer formation in the non-glandular region.

Additionally, the repetitive use of non-steroidal anti-inflammatory drugs (NSAIDs) such as phenylbutazone, flunixin meglumine, or ketoprofen may decrease the production of the protective mucus layer that provides the stomach a safety barrier from the gastric acid. This diminished protection increases susceptibility to ulcer formation.

The most recognized treatment for EGUS is Gastrogard® veterinary preparation. The active ingredient is omeprazole (marketed for humans as Prilosec® pharmaceutical preparation). Gastrogard® veterinary preparation is the only FDA-approved treatment for equine stomach ulcers. Because of the high rate of ulcer recurrence, either modified animal management strategies or ulcer prevention strategies must be employed. More recently, Ulcergard® veterinary preparation was introduced by Merial, Ltd. of Duluth, Ga., as a non-prescription, FDA-approved medication for prevention of gastric ulcers in horses. When horses previously administered Gastrogard did not achieve a cured status in ulcer score, subsequent Ulcergard® treatment produced highly variable and sometimes negative results. A 30-day treatment regimen of Gastrogard® veterinary preparation can cost between $1120 and $1680, depending upon dosage and individual veterinarian pricing, while the Ulcergard® veterinary preparation prevention programs cost between $300 and $360 per 28-day prevention program for horses between 600 and 1200 pounds of body weight.

Omeprazole is a proton pump inhibitor (PPI) that inhibits gastrointestinal acid secretion. Omeprazole is absorbed in the small intestine. A pharmaceutical oral solid dosage form of omeprazole must be protected from gastrointestinal acid so that it can pass to the small intestine. An enteric coating is often used to protect the active ingredient from degradation by stomach acid to maintain pharmaceutical activity.

Due to these high costs, many horse owners have sought out and purchased compounded variations of omeprazole paste or suspension products from their veterinarian. These are less expensive, costing approximately $200 to $240 per month for a preventative program. Unfortunately, these compounded formulations often lack efficacy. The efficacy and potency of omeprazole is difficult to maintain through the compounding process. Two recent studies have revealed that compounded omeprazole suspensions were ineffective in healing gastric ulcers in race horses.

Since ulcer recurrence is very problematic, horse owners have sought less expensive prevention programs that include the feeding of antacid-type additives to potentially protect their animals. These products include a wide variety of buffering and/or neutralizing compounds and/or mineral ingredients. These products have very mixed reviews, with little (if any) published scientific data to support inferences that the products prevent ulcer development or facilitate healing of gastric ulcers.

Other potential problems may limit the suitability of ingredients for use in antacid-type feed supplements:

A. Low capacity to neutralize meaningful amounts of gastric acid.

B. Reactivity rate is not proportional to retention time in the stomach.

C. Ability to be retained in the stomach beyond the gastric fluid turnover rate.

D. Palatability and general acceptability to oral and esophageal tissues.

Hydrochloric acid and volatile fatty acids contained in gastric fluids are strong acids. Weak bases, such as calcium carbonate, dicalcium phosphate, or magnesium oxide, cannot be fed in sufficient amounts to practically neutralize the excess acidity in the stomach environment and reduce the incidence of gastric ulcers. Additionally, the weak bases have limited solubility in water and their acid neutralizing capability is only moderate. They may be somewhat more effective in providing a degree of neutralizing capacity by the time they reach the lower tract than they are in the upper tract.

An effective neutralizing agent must possess the ability to be reactive in a time period that is proportional to the time it is present in the stomach. Horses exhibit a rapid turnover rate in stomach contents with liquid retention times as low as 15 to 60 minutes. Therefore, solubility and reactivity in a low pH environment at body temperature is critical.

If a horse consumes an antacid product at feeding time or is dosed with a suspension or paste product at another time, this ingredient can only be effective while it is present in the stomach. Most water-soluble buffer ingredients have a very short retention time (usually <60 minutes) in the stomach, leaving the horse relatively unprotected in only a short time after administration. Many of these weak base products would require 6-12 doses distributed through the day in order to be effective in providing protection from excessive gastric acidity.

Stronger bases such as sodium hydroxide, magnesium hydroxide, and calcium hydroxide are available and possess the capability to neutralize the strong acid effects in the stomach. However, they are generally highly unpalatable to the horse and can be damaging to tissues in the mouth and esophagus. If diluted to such an extent as to be palatable and tissue-friendly, their effectiveness is doubtful unless dosed in very large amounts at very frequent intervals.

Another complication for horse owners attempting to find non-prescription solutions to alleviate excess acidity in the stomach of their horses is the unexpected side effects of some of the ingredients found in particular equine antacid products.

U.S. Patent Application Publication No. 2005/0163867 discloses a composition for treating ulcers in mammals. The composition contains magnesium hydroxide (a strong base) as a primary active neutralizing ingredient. U.S. Pat. No. 6,284,265 discloses an equine antacid product, while specifically noting that magnesium hydroxide can produce an ataxic effect in horses at higher dosage rates.

There are also products that include aluminum compounds such as aluminum phosphate, aluminum hydroxide, and/or dihydroxy-aluminum-sodium-carbonate. The side effects for this group of compounds include reduced crude protein digestibility, increased urinary excretion of iron, reduced absorption of ferrous sulfate (a common source of iron in equine feeds), reduced phosphorus digestibility, and reduced gastrointestinal absorption of amino acids (building blocks of protein for the body).

There are also important negative ingredients/drug interactions from this group of aluminum compounds, including reduced gastrointestinal absorption of chlortetracycline, oxytetracycline, and tetracycline (important antibiotics in treating respiratory infections) and reduced bioavailability of prednisone (an important corticosteroid used in the treatment of severe allergies, skin disease, and arthritis). Additionally, in the case where ascorbic acid (vitamin C) has been included in the diet (contained in many commercial athletic and senior horse feeds), the ascorbic acid/aluminum phosphate interaction poses a high risk of excessive absorption of aluminum.

Therefore, there is a need for an effective lower cost composition and method for improving the gastrointestinal health in horses by reducing gastric ulcers. The composition should avoid negative interactions and side effects, while providing a straight forward delivery method.

SUMMARY OF THE INVENTION

The invention relates to various exemplary embodiments, including compositions, products, and methods of treatment, and of using the same.

These and other features and advantages of exemplary embodiments of the invention are described below with reference to the accompanying drawings.

DETAILED DESCRIPTION

Figure 1:
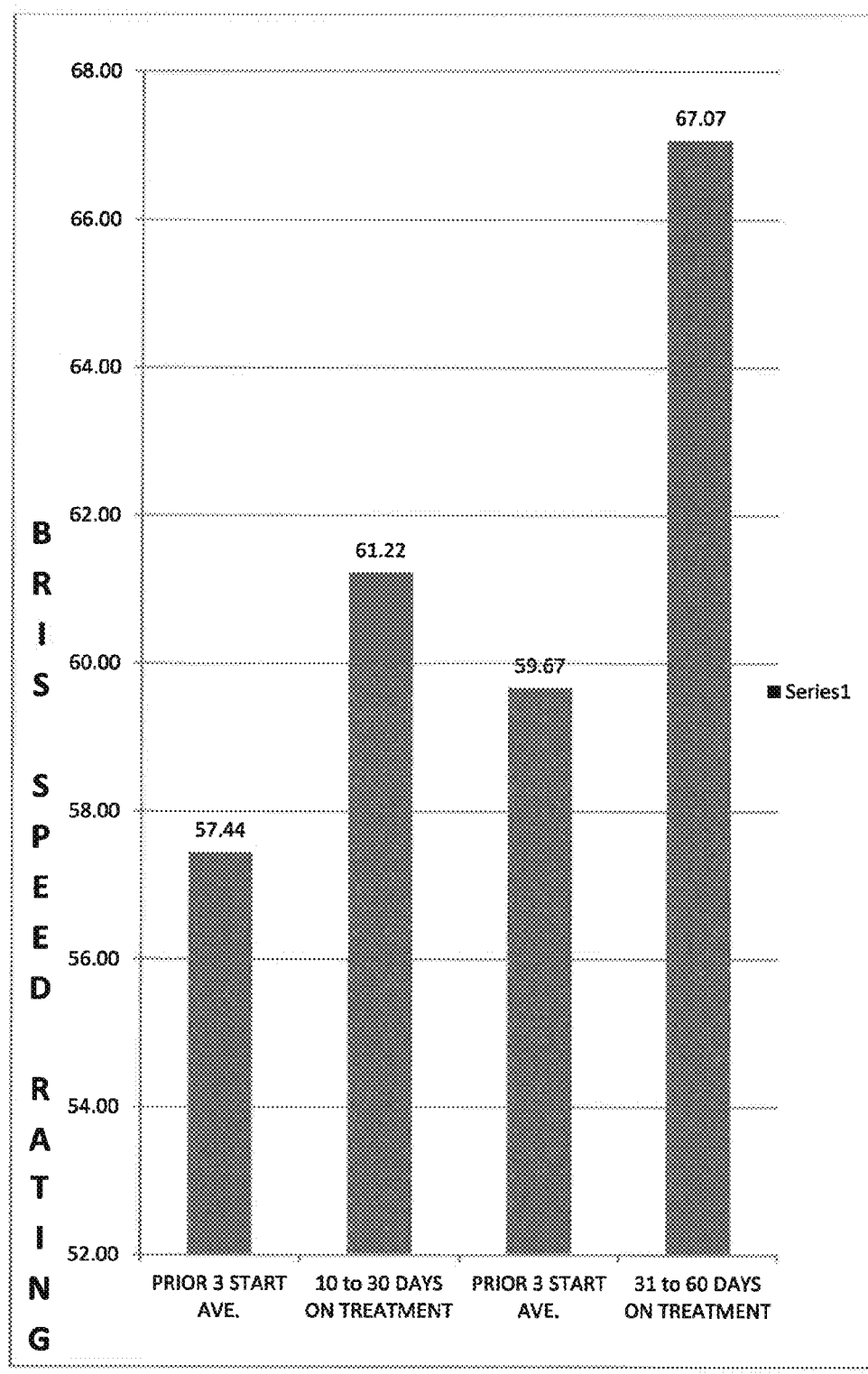
FIG. 1 shows the increase in BRIS Speed Ratings for horses after administration of the composition of the present invention.

In the following detailed description, numeric values and ranges are provided for various aspects of the implementations described. These values and ranges are to be treated as examples only and are not intended to limit the scope of the claims. In addition, a number of materials and ingredients are identified as suitable for various facets of the implementations. These materials and ingredients are to be treated as exemplary and are not intended to limit the scope of the claims.

The invention entails the combining of primary active ingredients with other ingredients to limit reactivity of the alkalizing agents in the oral and esophageal regions to prevent reduction in feed intake, improve palatability, and control premature chemical reactivity. By preserving the activity of the primary active ingredients in combination with other specifically selected and balanced materials, this composition neutralizes excess stomach acidity, buffers fluids and contents of the gastrointestinal tract, and exhibits itself as a bioactive agent for a positive effect on tissue repair.

In particular, the invention includes a metal hydroxide and a metal oxide that are minimally soluble in water, but reactive in stomach acid. In a particular implementation, the composition includes calcium hydroxide ($Ca(OH)_2$) and calcium oxide (CaO). The metal hydroxide and metal oxide are included in a composition that combines them with simple carbohydrates, vegetable oil, probiotics, and buffers in such a manner as to limit their reactivity in the oral and esophageal regions, thus preserving their acid neutralizing capability until reaching the stomach. Once in the stomach, the vegetable oil becomes disassociated and the simple carbohydrate is hydrolyzed away by the stomach acids. CaO is effective not only as an active ingredient, but particularly so because of the easy conversion of CaO to $Ca(OH)_2$ with the simple addition of water and time.

Additional ingredients, including absorbents (such as sodium bentonite), buffers, probiotics, and weaker bases and alkalizing agents can also be included in the composition. These ingredients can be selected and balanced in the concentration of the total composition by their solubility, rate of reactivity, and neutralizing capacity to affect particular focal points of the gastrointestinal tract. The primary metal hydroxide used in the composition is calcium hydroxide. Metal oxides useful with the composition include calcium oxide and magnesium oxide. Buffers and coating agents may include sodium bicarbonate and sodium sesquicarbonate. The composition may also include calcium carbonate. Simple carbohydrates may include sugars utilized in the coating process. Probiotics provide sources of *Lactobacillus* bacteria. Finally, omega-3 and omega-6 fatty acids (such as those found in canola oil) may provide nutritional components and properties contributing to the coating.

Ingredients in this composition may have a singular application or dual purpose applications. The essential alkalizing agent is calcium hydroxide; the calcium oxide is included as an acid neutralizer and as a precursor of additional calcium hydroxide. The sugars are included as coating constituents and for palatability enhancement. The canola oil provides essential omega-3 fatty acids and acts as an important component in the coating procedure. Sodium bicarbonate provides buffering activity in the stomach and acts in conjunction with the sugars and oil to form the coating. Oatmeal acts as the solid substrate to carry the coated material and as a flow agent. Sodium bentonite acts as an absorbant. The sodium sesquicarbonate provides additional stomach buffering capacity. The probiotic serves as a coating material and as an essential source of *Lactobacillus* bacteria. The magnesium sulfate serves as a water-soluble source of magnesium important in upper tract magnesium supply. Magnesium oxide and calcium carbonate provide slight upper tract activity and moderate acid controlling activity in the lower tract.

In general, the composition of the present invention includes the following components (in approximate percentages by weight). The chemically active ingredients of the composition include: alkalizing agents, such as calcium hydroxide and calcium oxide plus water—about 12 to 20%; buffers, such as sodium bicarbonate and sodium sesquicarbonate—about 10 to 15%; lower tract neutralizers, such as magnesium oxide and calcium carbonate—about 5 to 10%; and soluble magnesium source, such as magnesium sulfate—about 1 to 3%. The chemically inactive ingredients of the composition include: probiotic, such as a *Lactobacillus* source—about 5 to 10%; sugars, such as sucrose—about 15 to 25%; canola oil—about 10 to 20%; sodium bentonite—about 5 to 10%; and oatmeal—about 10 to 15%.

In use, the composition is administered to the animals two to four times daily to provide about 60 to 240 grams of the aforementioned composition per horse (about 900 to 1200 pounds of body weight) per 24-hour period.

It is necessary to provide a coating for the primary active ingredients to create an effective barrier between the tissues of the animals' oral cavities and the calcium hydroxide/calcium oxide. Several methods have been attempted and studied related to coatings, such as disclosed in U.S. Pat. No. 4,900,562 entitled "Feed Intake Limiting Composition Comprising Calcium Hydroxide for Cattle." The feed intake limiting method disclosed therein creates an oral sensitivity that encourages the animal to leave the feed stuff containing this additive to seek out water and other feed stuffs (forages) until that sensitivity subsides. The animal then returns for another small meal before departing again. The coating typically includes sugars, sodium bicarbonate, probiotic, and omega-3 and omega-6 fatty acids, such as in canola oil.

The nearly empty equine stomach is a hostile environment with a pH of about 1.5 to 2.0. Gastric hydrochloric acid is a strong acid and cannot be neutralized by practical amounts of weak bases such as metal carbonates and metal oxides. Calcium hydroxide ($Ca(OH)_2$) is a strong base and can be fed in modified form in smaller, more nutritionally responsible amounts, and it also contributes to the total calcium intake for the animal. Because of the hormone-mediated excretion and absorption of calcium, equine can optimally perform with a nominal excess of dietary calcium.

One of the ironies of feeding antacids with a portion of the daily grain mix to achieve consumption of an antacid composition is that during feeding, the animal has a reduced need for neutralization of excess stomach acid. During the feeding process, mastication stimulates saliva production, which is the most effective method possessed by the body of the horse to affect moderation of gastrointestinal pH, as the saliva furnishes an internally produced buffer. Additionally, the presence of food in the stomach dilutes the concentration of bile salts and their corrosive effects on the stomach.

With that being said, often horses' stomachs are mostly devoid of feedstuffs just prior to feeding; leading to a natural accumulation of gastric acid concentration. Also, as horses are animals of habit, they often anticipate meal time, creating additional production of gastric acid. Therefore, including a portion of the antacid as water-soluble, rapidly reactive reagents to combat this initial build-up of gastric acid at meal time is useful.

No other developer has utilized $Ca(OH)_2$ as a gastric acid neutralizing agent in the way contemplated herein, as none have utilized this ingredient nor suggested any method to overcome the feeding sensitivity issues. Calcium hydroxide provides the additional benefit of possessing substantial anti-microbial effects and a strong affinity and biocompatibility for soft tissue. This has been demonstrated by research in both humans and dogs where $Ca(OH)_2$ was utilized as a protective barrier in dental repair and treatment. In these trials involving damaged and/or infected tooth pulp (blood vessels, connective tissue, and nerves) and periapical tissue (tissue surrounding the apex of the root), $Ca(OH)_2$ expressed powerful anti-microbial action and significant stimulatory effect on regrowth of damaged tissue.

The affinity and biocompatibility of $Ca(OH)_2$ allows deposition on the stomach mucosa following ingestion of the antacid composition with a feed/grain meal. While there is substantial mixing of the stomach contents during and after feeding and the pH environment is most moderate due to the influx of saliva and dilution of bile salts by the feedstuffs, this allows for little erosion of the $Ca(OH)_2$ accumulation, until a point where the stomach is emptying and experiencing a measurable build up of gastric acid and subsequent pH decline. This decline in pH accelerates the reactivity of the $Ca(OH)_2$ with the gastric acids during times when the horse is most susceptible to stomach mucosal damage.

The active ingredients of the invention may be administered according to various methods known to those of skill in the art, including, but not limited to, a dry feed supplement, a liquid feed supplement, a liquid drench or emulsion, an oral paste formulation, or inclusion into a portion or all of the horse's daily grain or pelleted feed ration. This inclusion into the horses' daily feed may be accomplished by hand-mixing or by incorporation into the feed ingredients during or after the manufacturing process. The aforementioned composition is formulated for use as a dry feed supplement. Performance horses are normally fed their grain or feed in two or three meals spread throughout the day. At meal time, 50% of the recommended daily (120 gram) dosage, being 60 grams, is poured on to and mixed by hand into the feed before offering to the horse. This mixing procedure allows for even consumption of the composition and enhanced acceptability by the horse.

Another alternative for implementing the composition of the present invention is as follows. Most commercial horse feeds are pelleted or made up of pellets that are blended with grains and coated with molasses (textured). The pellet contents are usually made up of finely-ground grains, vegetable proteins, finely ground grain by-products, and other feed ingredients. A manufacturer could simply include calcium hydroxide and/or calcium oxide into the ground feed before pelleting, because the pelleting process involves injecting steam while subjecting the feedstuffs to pressure to form pellets, which additionally converts the calcium oxide to calcium hydroxide. By pelleting the active ingredients within the mixture, the surface area of the calcium hydroxide is greatly reduced, which may be a way of alleviating the oral contact issues of those active ingredients. While the result of including only the primary active ingredients would not be as effective as the complete composition, it could be as simple as including the appropriate amount (about 10 to 100 grams per horse per day) of calcium hydroxide and/or calcium oxide in each 2000 pound batch of ingredients prior to the pelleting process, depending on the daily amount fed, which may derive as much as 50% or more of the physical benefits in the horse. The amount added to each 2000 pound batch of ingredients would typically be about 5 to 50 pounds of calcium hydroxide and/or calcium oxide. In some implementations, about 10 to 30 pounds would be added to each 2000 pound batch.

EXAMPLE 1

If the target amount was 50 grams of calcium hydroxide/calcium oxide per horse per day and the feeding rate per horse was 10 pounds of feed per horse per day, then the calculation would be as follows: 2000 pound feed batch divided by the feeding rate (about 10 pounds per horse per day) equals 200 horses fed per 2000 pound batch of feed. 200 horses multiplied by 50 grams (the targeted daily amount of calcium hydroxide/calcium oxide per horse) equals 10,000 grams or 22 pounds of calcium hydroxide and/or calcium oxide to be added to each 2000 pound batch of horse feed.

EXAMPLE 2

In one example, the composition is formed with the following ingredients listed in percentage by weight:
Sugars—21
Calcium Oxide and Calcium Hydroxide—15.88
Canola Oil—15
Sodium Bicarbonate and Sodium Sesquicarbonate—14.12
Oatmeal—10
Probiotic—7
Magnesium Oxide—6.9
Sodium Bentonite—5
Magnesium Sulfate—3
Calcium Carbonate—2.1

To create the special coating for the primary alkalizing agent, the sugars are pulverized and then mixed in with a folding action while the oil is added to form an emulsion. The oatmeal is also added via a slow folding action to provide a solid substrate, which acts as the attractant for the calcium oxide and calcium hydroxide that is added during a slow paddle mixing procedure. After an agglomeration appearance is attained, the fine sodium bicarbonate and probiotic are added to the sticky mixture via a slow paddle mixer. After the mixture is thoroughly blended, sodium bentonite is slowly added to absorb any extraneous oil. In approximately 45 to 90 seconds, depending on weather conditions, the formulation begins to turn into a coarse, slightly flowable mash of various particle sizes. After stabilizing, the remaining ingredients are carefully blended in so as not to create any unnecessary friction in the mix.

The finished composition is a palatable, light beige mash made up of variably sized particles which are moderately flowable. A typical recommended dosage is 60 grams fed twice daily with the normal feed ration. The feeding rate may vary with the individual situation between 60 and 240 grams per horse per day.

In one particular administration regimen for 900 to 1300 pound horses, one half measure (approx. 30 grams) is fed to the horses twice daily by thorough mixing into each portion of the daily feed ration. After 7 days, the regimen is increased to a full measure (approx. 60 grams), which is thoroughly mixed into the daily feed ration twice daily. It is recommended to permit the horses to have access to forage or hay continuously and to provide fresh clean water at all times, except immediately after strenuous exercise.

Since excessive gastric acidity is the known precursor for EGUS, preventing development and/or preventing recurrence after treatment is of utmost importance. When horses experience this devastating syndrome, they often experience weight loss, reduced appetite, general discomfort, dull hair coat and reduced athletic performance. Most of these symptoms are difficult to measure objectively.

In an attempt to measure the benefit of this antacid composition, a field study was undertaken to determine a baseline performance level and subsequent changes in athletic performance. Horses were maintained on the same feeding and management schedules as in the prior pretreatment period, except for the addition of the trial composition to their feed twice daily. The addition of the trial composition was 60 grams, twice daily, measured by the volume of a pre-sized stainless steel cup. Twelve horses were evaluated by calculating the prior three race performances and averaging their BRIS speed rating to establish a baseline. Therefore, each horse served as his own control treatment. Then, we measured their subsequent race performance (BRIS Speed Ratings) during their races from 10-30 days after beginning treatment. Additionally, we measured their BRIS Speed Ratings during their races from 31-60 days after beginning treatment. The difference for the 10-30 day period was an increase of 3.78 BRIS Speed Points, which is equal to 2.5 lengths in Sprint Races and 3.78 lengths in Route Races. The difference for the 31-60 day period was an increase of 7.4 BRIS Speed Points, which is equal to 4.93 lengths in Sprint Races and 7.4 lengths in Route Races (See FIG. 1). The results demonstrate a significant improvement in athletic performance for the treated horses, which would be a good indicator of improved gastrointestinal health.

With the field study showing positive results from the composition inclusion on race horse performance, further research was indicated to confirm the possible mode of action. While improvement in gastrointestinal health was the most likely influence for the increased racing performance, further research was warranted to confirm this mode of action. A small controlled trial was undertaken to measure actual effects of the proprietary composition on gastrointestinal ulcers in live race horses with physical endoscopic exams performed by a skilled equine veterinarian. The treatments included the actual composition and a placebo of similar appearance and amount which were fed at 30 grams twice daily through a seven day acclimation period. The trial period feeding rate was at 60 grams twice daily mixed into the feed ration for both groups. The identities of the treatments were blinded to the examining veterinarian, trainers, and stable staff. An independent third party from a well-recognized regional university assigned the horses to their treatment groups, monitored procedures, and maintained quantitative measurements.

Twelve race horses in training with small, moderate, and severe ulcers were identified to participate. Equine gastric ulcers are scored on a scale of 1.0 to 4.0 based on their severity. This scale is well known in the art. Ulcer scores ranged from 1.0 to 4.0 across the total population.

Figure 2:
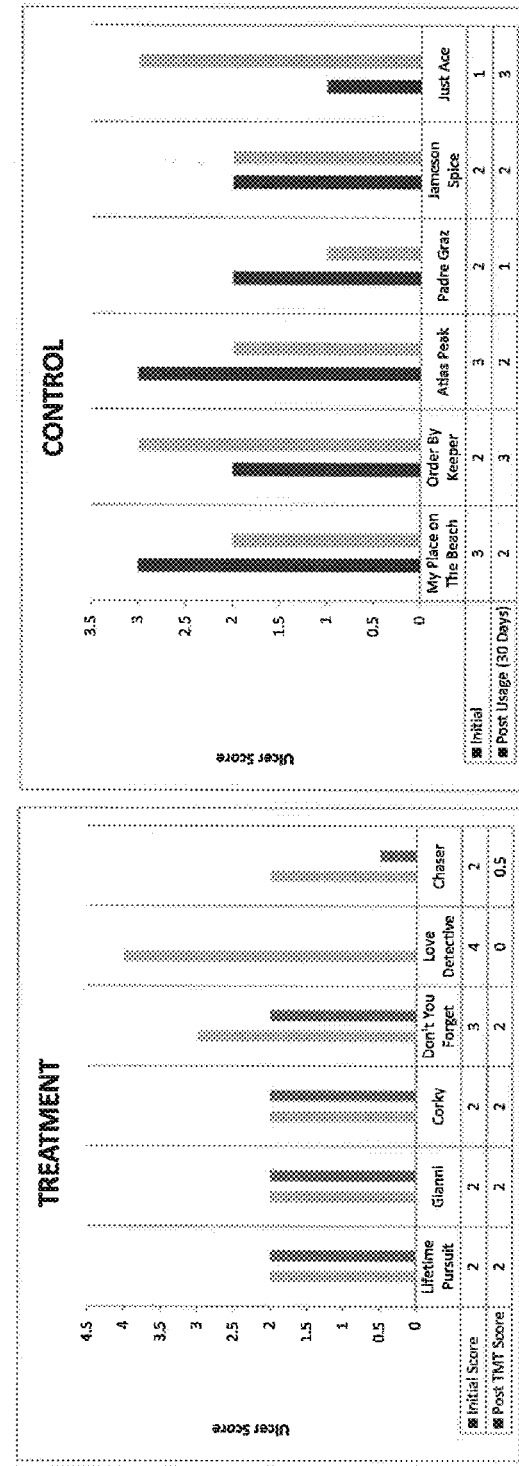
FIG. 2 shows results from a study where the composition according to the present invention was administered to horses.

The initial ulcer score average for the control (placebo) group was recorded at 2.17, while the treatment (composition) group was recorded at 2.5. The treatment (composition) group was treated with a composition according to the present invention. Following the acclimation and treatment periods, the control (placebo) group experienced both positive and negative changes within the group with no net effect on the average ulcer score for the group. Within the treatment (composition) group, none of the individual horses experienced an increase in ulcer score by trial completion. This strongly suggests an ability of the composition to prevent further gastric ulceration. The treatment (composition) group had an average ulcer score of 2.5 at trial initiation and an ulcer score of 1.42 by trial completion. This 1.08 reduction calculates to a 43.2% reduction in ulcer score, which is both biologically and economically significant. With demonstrated positive effects on animal performance and positive effects on measurable live animal ulcer scores, this cost effective composition has the potential to provide gastrointestinal benefits to a significantly larger proportion of the ulcer prone horse population. The results of this study are shown in FIG. 2.

Two additional studies in human dentistry indicate $Ca(OH)_2$ exhibiting itself as a bioactive agent for producing a positive effect on tissue engineering. $Ca(OH)_2$ also demonstrated an increase in DNA synthesis of tooth pulp cells. Therefore, repeated exposure of $Ca(OH)_2$ to damaged stomach mucosal cells should be considered beneficial for their regeneration and repair.

The FDA-approved omeprazole medications have proven to be effective; however, there have been treatment failures. In fact, the results of the study of the composition of the present invention, as shown in FIG. 2, have been better than the preventative (Ulcergard®) level studies with omeprazole. In studies of this type where omeprazole preventative compositions were administered to horses with incomplete responses to Gastrogard®, the horses often saw increased ulcer scores, rather than decreased scores. In some studies, 33% showed no improvement and even up to ⅔ of the horses had increased ulcer scores. By contrast, none of the horses in the study summarized in FIG. 2 had increased ulcer scores. In attempts to explain the occasional treatment failures with omeprazole in both man and horse, research studies on rats with ulcers were undertaken to determine if there were any underlying causes. In these studies, the rats with ulcers that responded poorly to the omeprazole treatments were sacrificed and, upon examination, the ulcer bed was often found to be colonized by bacteria. In subsequent experiments, where rats with ulcers were drenched with *E. coli* and then treated with omeprazole, they also healed more slowly. When half of the *E. coli* drenched rats with ulcers received *Lactobacillus* in addition to omeprazole, they healed normally. It is believed that the *Lactobacillus* competed with the *E. coli* in the ulcer bed, allowing the mucosa to heal. Importantly, the composition herein contains the full recommended rate of a premium *Lactobacillus* probiotic when fed at the 120 gram daily rate. This provides effective beneficial bacteria as a mechanism to displace harmful bacteria that may have invaded the damaged tissue in and around the ulcer bed of affected horses.

A particular implementation of the composition of the present invention includes the following ingredients: sucrose, canola oil, oat groats, calcium carbonate, magnesium oxide, magnesium sulfate, sodium bicarbonate, sodium bentonite, sodium sesquicarbonate, dried whey, calcium oxide, calcium hydroxide, sodium silico aluminate, sodium thiosulfate, dried *Enterococcus Faecium* fermentation product, dried *Lactobacillus Acidophilus* fermentation product, dried *Lactobacillus Casei* fermentation product, and dried *Lactobacillus Plantarum* fermentation product. An analysis of the product provided the following approximate percentages by weight:

| | |
|---|---|
| Calcium | 8.5% to 10.2% |
| Sodium | 2.9% to 3.4% |
| Magnesium | 3% |

While the invention has been described in conjunction with specific exemplary implementations, it is evident to those skilled in the art that many alternatives, modifications, and variations will be apparent in light of the foregoing description. Accordingly, the invention is intended to embrace all such alternatives, modifications, and variations that fall within the scope and spirit of the appended claims.

What is claimed is:
1. A palatable composition for increasing gastrointestinal pH of equine comprising:
   a substrate of oatmeal, wherein the oatmeal comprises about 10 to 15% by weight of the composition;
   about 12 to 20% by weight calcium hydroxide, calcium oxide, or a combination thereof;
   sodium bicarbonate, sodium sesquicarbonate, or a combination thereof;
   about 5 to 10% by weight magnesium oxide, calcium carbonate, or a combination thereof;
   about 1 to 3% by weight magnesium sulfate; and
   a coating that creates an effective barrier between tissue of the equine oral cavity and the calcium hydroxide and the calcium oxide, the coating comprising:
   about 15 to 25% by weight sucrose;
   sodium bicarbonate;
   about 5 to 10% by weight *Lactobacillus* source;
   about 10 to 20% by weight canola oil; and
   about 5 to 10% by weight sodium bentonite.

* * * * *